(12) United States Patent
Tateishi et al.

(10) Patent No.: US 11,529,078 B2
(45) Date of Patent: Dec. 20, 2022

(54) FLUID EVALUATION APPARATUS AND METHOD, COMPUTER PROGRAM, AND RECORDING MEDIUM

(71) Applicants: PIONEER CORPORATION, Tokyo (JP); NIKKISO COMPANY LIMITED, Tokyo (JP)

(72) Inventors: Kiyoshi Tateishi, Kawagoe (JP); Wataru Onodera, Kawagoe (JP); Atsuya Ito, Kawagoe (JP); Tomoya Murakami, Makinohara (JP); Akari Agata, Makinohara (JP); Genki Adachi, Makinohara (JP)

(73) Assignees: AIR WATER BIODESIGN INC., Hyogo (JP); NIKKISO COMPANY LIMITED, Tokyo (JP)

( * ) Notice: Subject to any disclaimer, the term of this patent is extended or adjusted under 35 U.S.C. 154(b) by 826 days.

(21) Appl. No.: 16/466,780

(22) PCT Filed: Dec. 5, 2016

(86) PCT No.: PCT/JP2016/086088
§ 371 (c)(1),
(2) Date: Jun. 5, 2019

(87) PCT Pub. No.: WO2018/105013
PCT Pub. Date: Jun. 14, 2018

(65) Prior Publication Data
US 2020/0077934 A1    Mar. 12, 2020

(51) Int. Cl.
| | |
|---|---|
| *A61B 5/145* | (2006.01) |
| *G01N 15/02* | (2006.01) |
| *G01N 21/53* | (2006.01) |
| *G01N 15/00* | (2006.01) |

(52) U.S. Cl.
CPC ...... *A61B 5/14535* (2013.01); *G01N 15/0211* (2013.01); *G01N 21/53* (2013.01); *G01N 2015/0065* (2013.01)

(58) Field of Classification Search
CPC . A61B 5/14535; G01N 15/0211; G01N 21/53
See application file for complete search history.

(56) References Cited

U.S. PATENT DOCUMENTS

| | | |
|---|---|---|
| 6,173,197 B1 | 1/2001 | Boggett et al. |
| 7,420,658 B2 | 9/2008 | Petterson et al. |
| (Continued) | | |

FOREIGN PATENT DOCUMENTS

| | | |
|---|---|---|
| EP | 2837327 A1 | 2/2015 |
| JP | 2016-146958 A | 8/2016 |
| (Continued) | | |

OTHER PUBLICATIONS

International Search Report, dated Jan. 10, 2017, from corresponding PCT application No. PCT/JP2016/086088.
(Continued)

*Primary Examiner* — Rebecca C Bryant
(74) *Attorney, Agent, or Firm* — Nixon & Vanderhye

(57) ABSTRACT

This fluid evaluation device is provided with an irradiation unit for irradiating a fluid with light, a light reception unit for receiving scattered light from the fluid and outputting a light reception signal, and an estimation unit for estimating at least one from among flow rate and density by mapping input points, which are on a first plane defined by flow rate and frequency and are expressed by light amount information indicating the amount of scattered light included in the light reception signal and frequency information indicating a frequency for a beat signal resulting from the Doppler
(Continued)

shifting of the light included in the light reception signal, onto a second plane defined by fluid flow rate and fluid density.

7 Claims, 11 Drawing Sheets

(56) References Cited

U.S. PATENT DOCUMENTS

| | | | |
|---|---|---|---|
| 2005/0243303 A1 | 11/2005 | Pettersson et al. | |
| 2008/0275320 A1 | 11/2008 | Pettersson et al. | |
| 2021/0396559 A1* | 12/2021 | Provost | G01F 1/663 |
| 2022/0039669 A1* | 2/2022 | Schlebusch | A61B 5/6869 |

FOREIGN PATENT DOCUMENTS

| | | | |
|---|---|---|---|
| WO | 2004/057313 A1 | 7/2004 | |
| WO | 2013/153664 A1 | 10/2013 | |
| WO | WO-2013153664 A1 * | 10/2013 | A61B 5/0261 |

OTHER PUBLICATIONS

Extended European Search Report issued in European Patent Application No. 16923446.5 dated Jun. 30, 2020.
Obeid, A.N., "In Vitro Comparison of Different Signal Processing Algorithms Used in Laser Doppler Flowmetry," Medical and Biological Engineering and Computing, vol. 31, No. 1, Jan. 1, 1993.

* cited by examiner (a)

(b)

(a)

(b)

FLUID EVALUATION APPARATUS AND METHOD, COMPUTER PROGRAM, AND RECORDING MEDIUM

TECHNICAL FIELD

The present invention relates to a fluid evaluation apparatus for and a fluid evaluation method of evaluating a fluid on the basis of a signal obtained by applying light to a fluid, such as, for example, a blood, which flows inside a measurement target, and by receiving the light from the fluid, as well as a computer program, and a recording medium on which the computer program is recorded.

BACKGROUND ART

For this type of apparatus, for example, there is proposed an apparatus in which a light emitting diode (LED) and a light receiving element are arranged around a medical tubing and in which hematocrit of a blood that flows in the medical tubing is measured from a light receiving signal (refer to Patent Literature 1). Alternatively, there is proposed an apparatus configured to apply laser light to a tubing in which a blood flows, and configured to correct a blood flow volume, which is calculated from a Doppler shift of the laser light, on the basis of a blood concentration calculated from an amount of light received by the light receiving element (refer to Patent Literature 2).

CITATION LIST

Patent Literature

Patent Literature 1: WO 2004/057313 A1
Patent Literature 2: WO 2013/153664 A1

SUMMARY OF INVENTION

Technical Problem

The technologies/techniques described in the Patent Literatures 1 and 2 have such a technical problem that an accurate result is likely not obtained if the amount of the light received is relatively small.

It is therefore an object of the present invention to provide a fluid evaluation apparatus and a fluid evaluation method that can appropriately evaluate a fluid, as well as a computer program and a recording medium.

Solution to Problem

The above object of the present invention can be achieved by a first fluid evaluation apparatus provided with: an irradiator configured to irradiate a fluid with light; a light receiver configured to receive scattered light from the fluid and configured to output a light receiving signal; and an estimator configured to map an input point that is on a first plane defined by a light amount and a frequency, on a second plane defined by a flow volume of the fluid and a concentration of the fluid, thereby estimating at least one of the flow volume and the concentration, wherein the light amount and the frequency are respectively indicated by light amount information, which indicates the light amount of the scattered light included in the light receiving signal, and by frequency information, which indicates the frequency associated with a beat signal caused by a Doppler shift of the light included in the light receiving signal.

The above object of the present invention can be achieved by a second fluid evaluation apparatus provided with: an irradiator configured to irradiate a fluid with light; a light receiver configured to receive scattered light from the fluid and configured to output a light receiving signal; and an estimator configured to transform a first parameter with light amount information and frequency information as components, to a second parameter with a flow volume of the fluid and a concentration of the fluid as components, thereby estimating at least one of the flow volume and the concentration, wherein the light amount information indicates a light amount of the scattered light included in the light receiving signal, and the frequency information indicates a frequency associated with a beat signal caused by a Doppler shift of the light included in the light receiving signal.

The above object of the present invention can be achieved by a fluid evaluation method in a fluid evaluation apparatus including: an irradiator configured to irradiate a fluid with light; and a light receiver configured to receive scattered light from the fluid and configured to output a light receiving signal, the fluid evaluation method provided with: an estimating process of mapping an input point that is on a first plane defined by a light amount and a frequency, on a second plane defined by a flow volume of the fluid and a concentration of the fluid, thereby estimating at least one of the flow volume and the concentration, wherein the light amount and the frequency are respectively indicated by light amount information, which indicates the light amount of the scattered light included in the light receiving signal, and by frequency information, which indicates the frequency associated with a beat signal caused by a Doppler shift of the light included in the light receiving signal.

The above object of the present invention can be achieved by a computer program for making a computer, which is provided in a fluid evaluation apparatus including: an irradiator configured to irradiate a fluid with light; and a light receiver configured to receive scattered light from the fluid and configured to output a light receiving signal, function as: an estimator configured to map an input point that is on a first plane defined by a light amount and a frequency, on a second plane defined by a flow volume of the fluid and a concentration of the fluid, thereby estimating at least one of the flow volume and the concentration, wherein the light amount and the frequency are respectively indicated by light amount information, which indicates the light amount of the scattered light included in the light receiving signal, and by frequency information, which indicates the frequency associated with a beat signal caused by a Doppler shift of the light included in the light receiving signal.

The above object of the present invention can be achieved by a recording medium on which the computer program of the present invention is recorded.

The effect of the present invention and other benefits will become apparent from the following description of embodiments.

DESCRIPTION OF EMBODIMENTS

Figure 1:
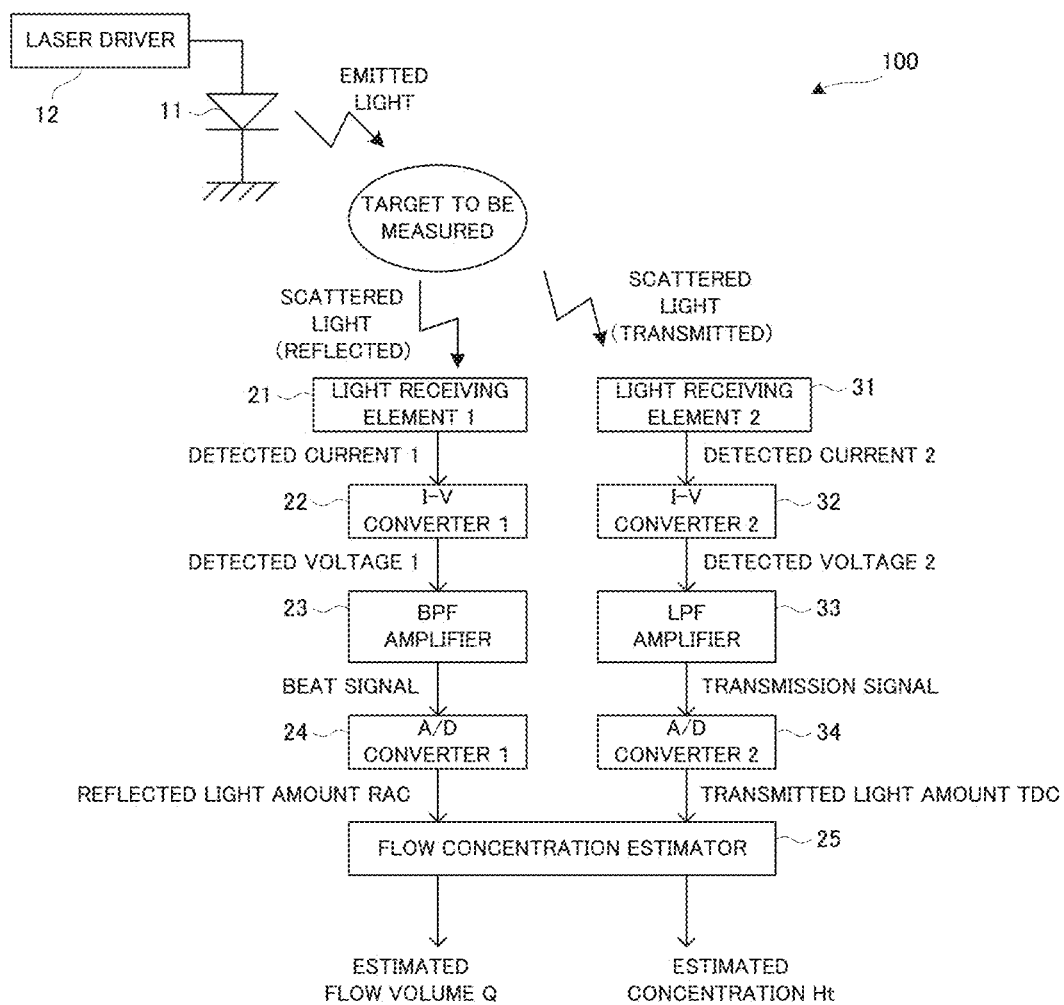
FIG. 1 is a block diagram illustrating a configuration of a fluid evaluation apparatus according to a practical example.

A fluid evaluation apparatus, a fluid evaluation method, a computer program, and a recording medium according to embodiments of the present invention will be explained.
(Fluid Evaluation Apparatus)
<First Embodiment>

A fluid evaluation apparatus according to a first embodiment is provided with: an irradiator configured to irradiate a fluid with light; a light receiver configured to receive scattered light from the fluid and configured to output a light receiving signal; and an estimator configured to map an input point that is on a first plane defined by a light amount and a frequency, on a second plane defined by a flow volume of the fluid and a concentration of the fluid, thereby estimating at least one of the flow volume and the concentration, wherein the light amount and the frequency are respectively indicated by light amount information, which indicates the light amount of the scattered light included in the light receiving signal, and by frequency information, which indicates the frequency associated with a beat signal caused by a Doppler shift of the light included in the light receiving signal.

According to the fluid evaluation apparatus, the input point on the first plane defined by the light amount and the frequency (in other words, including an axis indicating the light amount and an axis indicating the frequency) is mapped on the second plane defined by the flow volume and the concentration (in other words, including an axis indicating the light amount and an axis indicating the concentration). For example, a transformation coefficient associated with the mapping from the first plane to the second plane is known, and thus, if the input point on the first plane is specified, at least one of the flow volume and the concentration corresponding to the input point is obtained. Therefore, according to the fluid evaluation apparatus, the fluid can be appropriately evaluated.

In an aspect of the fluid evaluation apparatus according to the first embodiment, the estimator has lattice point information associated with a plurality of lattice points each of which has a known correspondence between a position indicated by the light amount and the frequency on the first plane and a position indicated by the flow volume and the concentration on the second plane. The estimator is configured to map the input point on the second plane, on the basis of a positional relation between the input point on the first plane and a lattice point indicated by the lattice point information.

In this aspect, the estimator may be configured to specify an area to which the input point belongs, from among one or a plurality of areas defined by a plurality of lattice points indicated by the lattice point information from the positional relation, and may be configured to map the input point on the second plane by using a transformation coefficient according to the specified area. According to this aspect, it is possible to map the input point from the first plane to the second plane, relatively easily. In another aspect of the fluid evaluation apparatus according to the first embodiment, the light receiver has a first light receiver configured to receive scattered light that is reflected by the fluid, out of the scattered light, and a second light receiver configured to receive scattered light that is transmitted through the fluid, out of the scattered light, and the estimator is configured to obtain the frequency information from an output signal of the first light receiver, which is a part of the light receiving signal, and is configured to obtain the light amount information from an output signal of the second light receiver, which is another part of the light receiving signal. According to this aspect, it is possible to obtain the light amount information and the frequency information, relatively easily.
<Second Embodiment>

A fluid evaluation apparatus according to a second embodiment is provided with: an irradiator configured to irradiate a fluid with light; a light receiver configured to receive scattered light from the fluid and configured to output a light receiving signal; and an estimator configured to transform a first parameter with light amount information and frequency information as components, to a second parameter with a flow volume of the fluid and a concentration of the fluid as components, thereby estimating at least one of the flow volume and the concentration, wherein the light amount information indicates a light amount of the scattered light included in the light receiving signal, and the frequency information indicates a frequency associated with a beat signal caused by a Doppler shift of the light included in the light receiving signal.

According to the fluid evaluation apparatus in the second embodiment, as in the fluid evaluation apparatus in the first embodiment, the fluid can be appropriately evaluated.

(Fluid Evaluation Method)

A fluid evaluation method is a fluid evaluation method in a fluid evaluation apparatus including: an irradiator configured to irradiate a fluid with light; and a light receiver configured to receive scattered light from the fluid and configured to output a light receiving signal. The fluid evaluation method is provided with: an estimating process of mapping an input point that is on a first plane defined by a light amount and a frequency, on a second plane defined by a flow volume of the fluid and a concentration of the fluid, thereby estimating at least one of the flow volume and the concentration, wherein the light amount and the frequency are respectively indicated by light amount information, which indicates the light amount of the scattered light included in the light receiving signal, and by frequency information, which indicates the frequency associated with a beat signal caused by a Doppler shift of the light included in the light receiving signal.

According to the fluid evaluation method in the embodiment, as in the fluid evaluation apparatus in the first embodiment, the fluid can be appropriately evaluated. The fluid evaluation method according to the embodiment can also adopt the same various aspects as those of the fluid evaluation apparatus according to the first embodiment described above.

(Computer Program)

A computer program according to an embodiment makes a computer, which is provided in a fluid evaluation apparatus including: an irradiator configured to irradiate a fluid with light; and a light receiver configured to receive scattered light from the fluid and configured to output a light receiving signal, function as: an estimator configured to map an input point that is on a first plane defined by a light amount and a frequency, on a second plane defined by a flow volume of the fluid and a concentration of the fluid, thereby estimating at least one of the flow volume and the concentration, wherein the light amount and the frequency are respectively indicated by light amount information, which indicates the light amount of the scattered light included in the light receiving signal, and by frequency information, which indicates the frequency associated with a beat signal caused by a Doppler shift of the light included in the light receiving signal.

According to the computer program in the embodiment, the fluid evaluation apparatus according to the first embodiment described above can be relatively easily realized by making the computer, which is provided in the fluid evaluation apparatus, execute the computer program. As a result, according to the computer program in the embodiment, as in the fluid evaluation apparatus according to the first embodiment described above, it is possible to appropriately evaluate the fluid.

(Recording Medium)

On a recording medium according to an embodiment, the computer program according to the embodiment described above is recorded. The fluid evaluation apparatus according to the first embodiment described above can be relatively easily realized as the computer provided in the fluid evaluation apparatus reads and executes the computer program recorded on a compact disc read only memory (CD-ROM), a DVD read only memory (DVD-ROM), or the like, which is an example of the recording medium according to the embodiment. As a result, according to the recording medium in the embodiment, as in the fluid evaluation apparatus according to the first embodiment described above, it is possible to appropriately evaluate the fluid.

Practical Example

A fluid evaluation apparatus according to a practical example of the present invention will be explained with reference to the drawings. In the practical example below, an example of the fluid is a blood that flows in a tubing that constitutes a blood circuit of an artificial dialysis apparatus.

(Configuration of Fluid Evaluation Apparatus)

Figure 2:
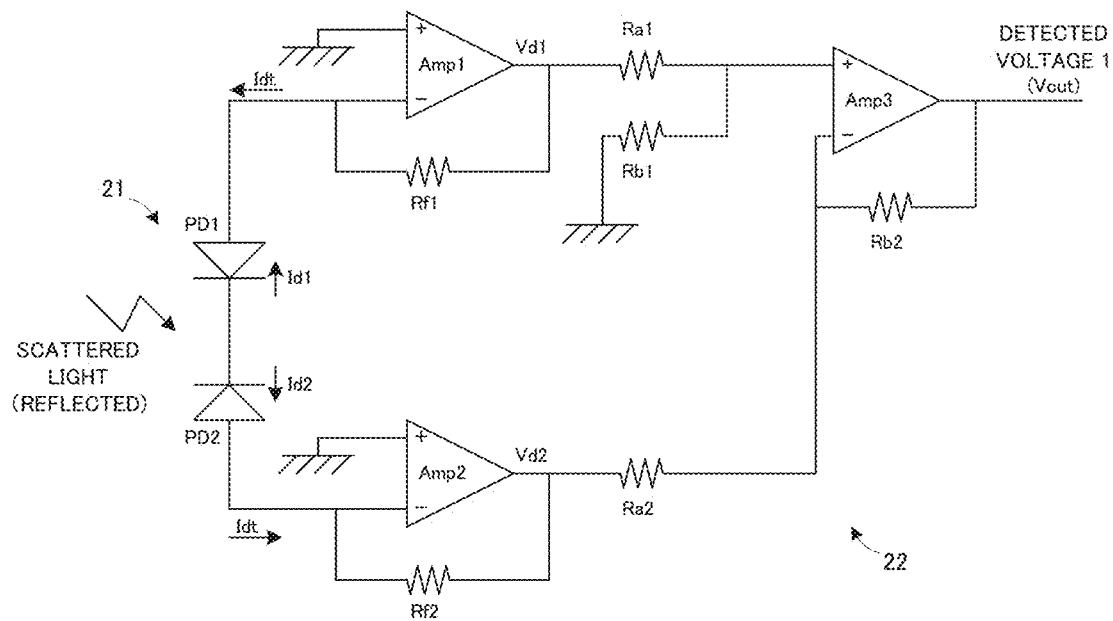
FIG. 2 is a circuit diagram illustrating an example of a light receiving element 21 and an I-V converter 22 according to the practical example.
Figure 3:
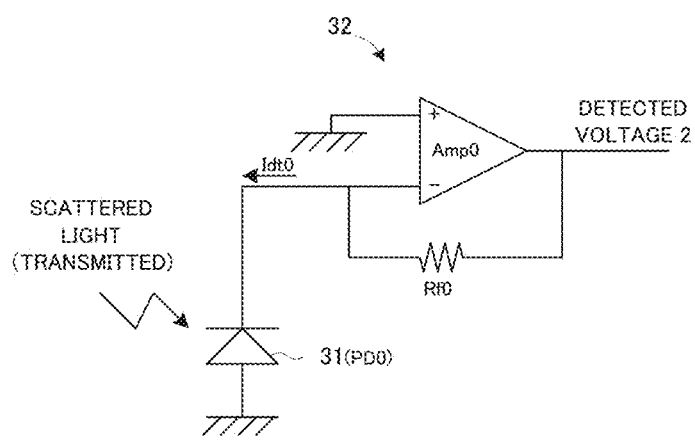
FIG. 3 is a circuit diagram illustrating an example of a light receiving element 31 and an I-V converter 32 according to the practical example.
Figure 4:
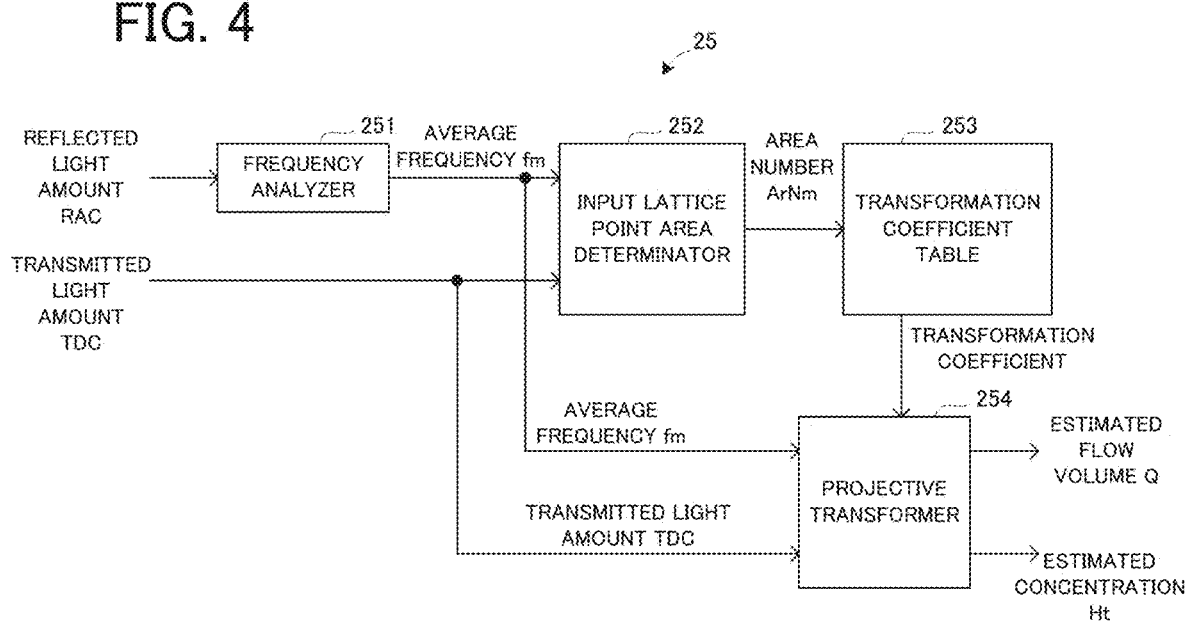
FIG. 4 is a block diagram illustrating a configuration of a fluid concentration estimator according to the practical example.
Figure 5:
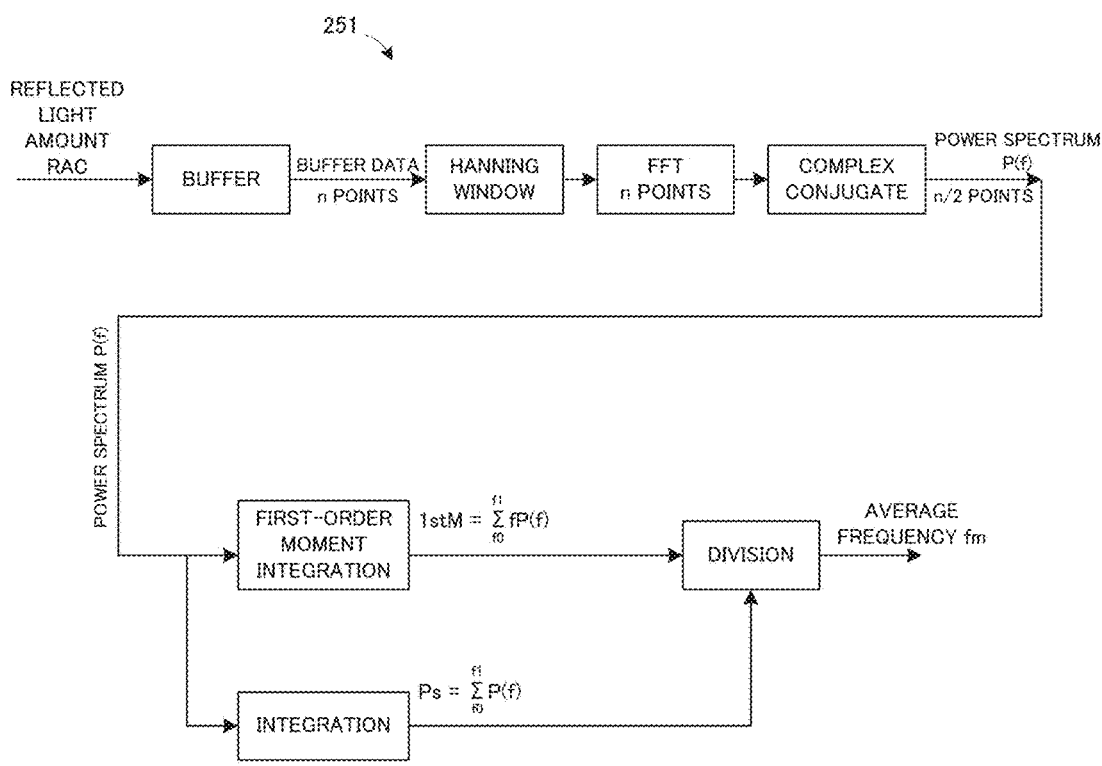
FIG. 5 is a conceptual diagram illustrating an example of frequency analysis.

A configuration of the fluid evaluation apparatus according to the practical example will be explained with reference to FIG. 1 to FIG. 5. FIG. 1 is a block diagram illustrating the configuration of the fluid evaluation apparatus according to the practical example. FIG. 2 is a circuit diagram illustrating an example of a light receiving element 21 and an I-V converter 22 according to the practical example. FIG. 3 is a circuit diagram illustrating an example of a light receiving element 31 and an I-V converter 32 according to the practical example. FIG. 4 is a block diagram illustrating a configuration of a fluid concentration estimator according to the practical example. FIG. 5 is a conceptual diagram illustrating an example of frequency analysis.

In FIG. 1, a fluid evaluation apparatus 100 is provided with a semiconductor laser 11, a laser driver 12, light receiving elements 21 and 31, I-V converters 22 and 32, a band-pass filter (BPF) amplifier 23, analog to digital (A/D) converters 24 and 34, a fluid concentration estimator 25, and a low-pass filter (LPF) amplifier 33.

The laser driver 12 is configured to generate an electric current for driving the semiconductor laser 11 (specifically, a specified drive current that is greater than or equal to a threshold current of the semiconductor laser 11). The semiconductor laser 11 is configured to perform laser oscillation in accordance with the drive current generated by the laser driver 12. An extracorporeal circulation blood circuit, which is a target to be measured (i.e., a transparent tubing in which a blood flows), is irradiated with laser light emitted from the semiconductor laser 11, via an optical system (not illustrated), such as, for example, a lens element. The irradiation laser light is scattered and absorbed by the tubing that constitutes the extracorporeal circulation blood circuit and by the blood that flows inside the tubing.

The extracorporeal circulation blood circuit may be semi-fixed to a casing (not illustrated) in which the semiconductor laser 11 and the light receiving elements 21 and 31 are mounted and fixed, so that an irradiation position is not shifted due to vibration or the like.

(i) Reflected Light

The light receiving element 21 is configured to receive reflected light including scattered light of the laser light with which the target to be measured is irradiated (which is herein backscattered light). The light receiving element 21 is configured to output a detected current (refer to "DETECTED CURRENT 1" in FIG. 1), which corresponds to intensity of the received scattered light and which is an example of the "light receiving signal" according to the present invention. The I-V converter 22 is configured to convert the detected current outputted from the light receiving element 21, to a voltage signal (refer to "DETECTED VOLTAGE 1" in FIG. 1).

The scattered light that enters the light receiving element 21 may include scattered light scattered by a structure that stands still (e.g., the tubing that constitutes the extracorporeal circulation blood circuit, etc.) and scattered light scattered by red blood cells included in the blood, which is a moving object. In the scattered light scattered by the red blood cells, the Doppler shift corresponding to a moving velocity of the red blood cells occurs.

Thus, the scattered light scattered by the structure that stands still and the scattered light scattered by the red blood cells interfere due to coherence of the laser light. The detected current outputted from the light receiving element 21 may include a beat signal that results from this interference.

The BPF amplifier 23 is configured to cut a frequency band of signal components, other than a predetermined frequency band of signal components, which is included in the voltage signal outputted from the I-V converter 22, and is configured to amplify the rest. Specifically, the BPF amplifier 23 may cut a low-frequency signal, such as, for example, a hum signal, and a high-frequency signal, such as, for example, a switching power supply noise, and may amplify and output a beat signal corresponding to the predetermined frequency band of signal components.

The A/D converter 24 is configured to perform an A/D conversion process (i.e., a quantization process) on the beat signal outputted from the BPF amplifier 23 and is configured to output a reflected light amount RAC, which is the quantified beat signal.

(ii) Transmitted Light

The light receiving element 31 is configured to receive transmitted light including scattered light of the laser light with which the target to be measured is irradiated (which is herein forward-scattered light). The scattered light received by the light receiving element 31 may include scattered light scattered by the blood that flows in the tubing that constitutes the extracorporeal circulation blood circuit (or particularly, the red blood cells, which are moving scatterers and which are included in the blood) and scattered light scattered by the structure that stands still, such as the tubing.

The light receiving element 31 is configured to output a detected current (refer to "DETECTED CURRENT 2" in FIG. 1), which corresponds to the intensity of the received scattered light and which is another example of the "light receiving signal" according to the present invention. The I-V converter 32 is configured to convert the detected current outputted from the light receiving element 31, to a voltage signal (refer to "DETECTED VOLTAGE 2" in FIG. 1).

The LPF amplifier 33 is configured to cut a frequency band of signal components, other than low-frequency signal components, which is included in the voltage signal outputted from the I-V converter 32, and is configured to amplify the rest. Moreover, the LPF amplifier 33 may perform band limitation to reduce an aliasing noise in the A/D converter 34. Here, the voltage signal outputted from the I-V converter 32 may include a high-frequency signal, which is a noise component, such as, for example, a switching power supply noise. The voltage signal outputted from the I-V converter 32 is inputted to the LPF amplifier 33, by which the signal can be amplified while the noise component is suppressed.

The A/D converter 34 is configured to perform the A/D conversion process on a transmission signal, which is a signal outputted from the LPF amplifier 33 (refer to "TRANSMISSION SIGNAL" in FIG. 1) and is configured to output a transmitted light amount TDC, which is the quantified transmission signal.

(iii) Estimator

The fluid concentration estimator 25 is configured to estimate at least one of a flow volume Q of the blood and a concentration Ht (which is a hematocrit value in the practical example), on the basis of the reflected light amount RAC and the transmitted light amount TDC. The details of an estimation method will be described later.

A Specific Example of Light Receiving Element 21 and I-V Converter 22

Next, an example of the light receiving element 21 and the I-V converter 22 will be explained with reference to FIG. 2.

In FIG. 2, the light receiving element 21 is provided with photodetectors PD1 and PD2, which are, for example, PIN type semiconductors. As illustrated in FIG. 2, a cathode of the photodetector PD1 and a cathode of the photodetector PD2 are connected. In other words, the photodetectors PD1 and PD2 are connected in series opposite to each other.

The I-V converter 22 is provided with amplifiers Amp1, Amp2, and Amp3, feedback resistors Rf1 and Rf2, and resistors Ra1, Rb1, Ra2, and Rb2.

An anode of the photodetector PD1 is connected to an inverting input terminal of the amplifier Amp1. A non-inverting input terminal of the amplifier Amp1 is connected to a reference potential, such as, for example, a ground potential. An anode of the photodetector PD2 is connected to an inverting input terminal of the amplifier Amp2. A non-inverting input terminal of the amplifier Amp2 is connected to the reference potential, such as, for example, a ground potential. An output of the amplifier Amp1 is inputted to a non-inverting input terminal of the amplifier Amp3. An output of the amplifier Amp2 is inputted to an inverting input terminal of the amplifier Amp3.

If the light receiving element 21 is configured in the above manner, it is possible to reduce or remove a DC component corresponding to a fixed or stationary light component included in scattered lights that enter the photodetectors PD1 and PD2, out of electric currents outputted from the photodetectors PD1 and PD2. On the other hand, it is possible to output an electric current that mainly includes an alternate current (AC) component corresponding to a signal light component included in the scattered light that enters, as the detected current.

Specifically, suppose that an output current of the photodetector PD1 is Id1 and an output current of the photodetector PD2 is Id2. The photodetectors PD1 and PD2 are connected in series with their polarities opposite to each other. Thus, the detected current by the light receiving element 21 is given by $$Idt = Id2 - Id1 \quad (1)$$

The scattered light received by the photodetector PD1 and the scattered light received by the photodetector PD2 may provide current signals that have almost no correlation, because they have different paths from each other when the wavelength of light is set as a reference length. Thus, the subtraction as in the equation (1) may result in $\sqrt{2}$ times the intensity of the beat signal. On the other hand, the DC component included in the output current may be canceled by the subtraction.

The light receiving element 21 can efficiently detect the beat signal as the AC component, while canceling the DC component of the output current of the photodetector PD1 and the DC component of the output current of the photodetector PD2.

As described above, because the DC component is reduced or removed, saturation can be prevented even if detection sensitivity of the amplifiers Amp1 and Amp2 is set relatively high, wherein the amplifiers Amp1 and Amp2 constitute the I-V converter 22 and the amplifiers Amp1 and Amp2 are so-called transimpedance amplifiers. Specifically, resistance values of the feedback resistors Rf1 and Rf2 can be set relatively high, and current-voltage conversion sensitivity can be improved. As a result, it is possible to improve a detection signal to noise ratio (S/N ratio).

As described above, the non-inverting input terminals of the amplifiers Amp1 and Amp2 are connected to the reference potential. By the action of negative feedback of the feedback resistor Rf1 or Rf2, the non-inverting input terminal and the inverting input terminal of each of the amplifiers Amp1 and Amp2 are in an imaginary-short state and have substantially the same potential.

As a result, the anode of the photodetector PD1 and the anode of the photodetector PD2 have the same potential, and the photodetectors PD1 and PD2 operate in a so-called power generation mode. The so-called power generation mode can prevent dark current and can prevent a noise caused by fluctuation of the dark current.

An output voltage Vd1 outputted from the amplifier Amp1 is given by $$Vd1 = Rf1 \cdot Idt \quad (2).$$

An output voltage Vd2 outputted from the amplifier Amp2 is given by $$Vd2 = -Rf2 \cdot Idt \quad (3).$$

The amplifier Amp3 is configured to differentially amplify the output voltages Vd1 and Vd2 and is configured to output a detected voltage Vout. Due to the differential amplification, an in-phase noise, such as, for example, a power supply noise and a hum, is removed.

If the resistor Ra1 and the resistor Ra2 are set to have a resistance value Ra and the resistor Rb1 and the resistor Rb2 are set to have a resistance value Rb, the detected voltage Vout can be given by $$Vout = (Rb/Ra)(Vd1 - Vd2) \quad (4).$$

If the feedback resistor Rf1 and the feedback resistor Rf2 are set to have a resistance value Rf, the detected voltage Vout can be given, from the equations (2), (3), and (4), by $$Vout = 2Rf(Rb/Ra)Idt \quad (5).$$

A Specific Example of Light Receiving Element 31 and I-V Converter 32

Next, an example of the light receiving element 31 and the I-V converter 32 will be explained with reference to FIG. 3.

In FIG. 3, the light receiving element 31 is provided with a photodetector PD0, which is, for example, a PIN type semiconductor. The I-V converter 32 is provided with an amplifier Amp0 and a feedback resistor Rf0. The amplifier Amp0 constitutes a so-called transimpedance amplifier.

An anode of the photodetector PD0 is connected to the reference potential, such as, for example, a ground potential. A cathode of the photodetector PD0 is connected to an inverting input terminal of the amplifier Amp0. A non-inverting input terminal of the amplifier Amp0 is connected to the reference potential, such as, for example, a ground potential.

An electric current Idt0 outputted from the photodetector PD0 is converted to a voltage by the feedback resistor Rf0 and is outputted from the amplifier Amp0 as the detected voltage (i.e., the voltage signal).

Configuration of Fluid Concentration Estimator

Next, a configuration of the fluid concentration estimator 25 will be explained with reference to FIG. 4.

In FIG. 4, the fluid concentration estimator 25 is provided with a frequency analyzer 251, an input lattice point area determinator 252, a transformation coefficient table 253, and a projective transformer 254.

The frequency analyzer 251 is configured to perform frequency analysis, such as fast fourier transform (FFT), on the reflected light amount RAC, and is configured to output an average frequency fm.

Now, a specific example of the frequency analysis will be explained with reference to FIG. 5. In FIG. 5, the reflected light amount RAC outputted from the A/D converter 24 is stored in a buffer, which includes a memory or the like, of the frequency analyzer 251. A capacity of the buffer corresponds to, for example, the number n of points for performing FFT.

A preliminary process for performing FFT is performed (refer to "HANNING WINDOW" in FIG. 5) on buffer data, which is an output from the buffer. Then, a FFT calculation for n points is performed on the data restricted by a window function of the Hanning window (refer to "FFT" in FIG. 5). A complex conjugate process is performed on a result of the FFT calculation (refer to "COMPLEX CONJUGATE" in FIG. 5), and data of n/2 points is outputted as a power spectrum P(f).

Then, the power spectrum P(f) and a frequency vector f are multiplied and integrated in a defined band (which is f0 to f1 herein), by which $1stM = \Sigma\{f \cdot P(f)\}$ is outputted as a first-order moment (refer to "FIRST-ORDER MOMENT INTEGRATION" in FIG. 5). In parallel with the output of the first-order moment, the power spectrum P(f) is integrated in the defined band (which is f0 to f1 herein), and $Ps = \Sigma\{P(f)\}$ is outputted (refer to "INTEGRATION" in FIG. 5). Then, a value obtained by dividing the first-order moment 1stM by Ps is outputted as the average frequency fm (refer to "DIVISION" in FIG. 5).

(Problems of Fluid Evaluation)

Before explaining fluid evaluation according to the practical example (i.e., estimation of the flow volume and the concentration), problems of the fluid evaluation will be explained with reference to FIG. 6 to FIG. 11.

Figure 6:
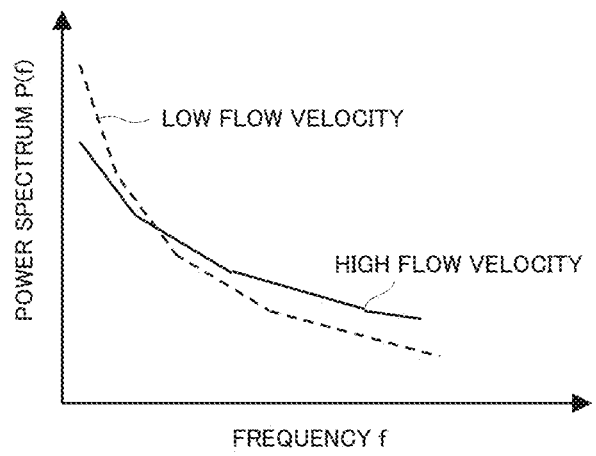
FIG. 6 is a diagram illustrating an example of a relation between frequency and a power spectrum P(f).

As illustrated in FIG. 6, when the blood has a relatively low flow velocity, (i.e., when the red blood cells, which are the scatterers that flow in the tubing that constitutes the extracorporeal circulation blood circuit, have a relatively slow flow velocity, the degree of the low-frequency component is much greater than that of the high-frequency component (refer to a dashed line in FIG. 6). On the other hand, when the blood has a relatively high flow velocity, (i.e., when the red blood cells have a relatively fast flow velocity, the degree of the high-frequency component is relatively high (refer to a solid line in FIG. 6).

This is because if a moving body (which is the red blood cells herein) has a high velocity, a Doppler shift amount increases and a relatively high frequency area component increases in a frequency spectrum characteristic of the beat signal. Therefore, as the velocity of the red blood cells flowing (i.e., the flow velocity of the fluid) increases, the average frequency fm increases (refer to FIG. 7).

Figure 8:
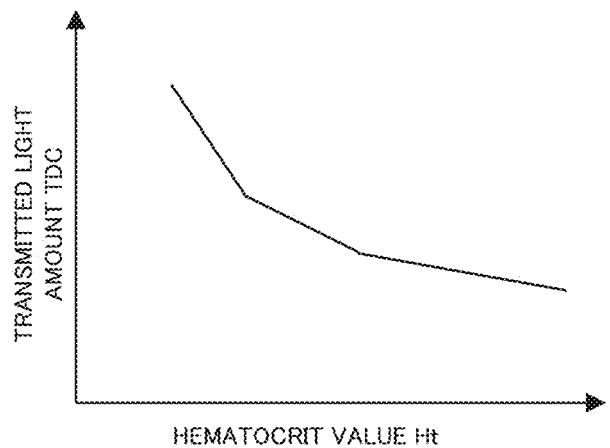
FIG. 8 is a diagram illustrating an example of a relation between a hematocrit value Ht and a transmitted light amount TDC.

Moreover, as illustrated in FIG. 8, if the concentration of the blood increases (i.e., if the hematocrit value increases), the transmitted light amount TDC is attenuated due to an increase in light scattering and absorption caused by the red blood cells.

Figure 7:
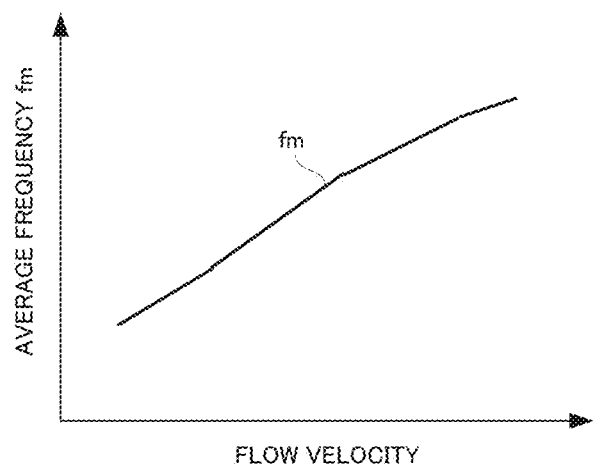
FIG. 7 is a diagram illustrating an example of a relation between a flow velocity and an average frequency fm.

If only the graphs illustrated in FIG. 7 and FIG. 8 are seen, it seems that the flow volume of the fluid can be obtained from the average frequency fm and that the concentration of the fluid can be obtained from the transmitted light amount TDC. According to studies by the present inventors, however, it is found that the average frequency fm depends not only on the flow velocity but also on the concentration of the fluid including the scatterers, and it is also found that the transmitted light amount TDC depends not only on the concentration but also on flow velocity of the fluid including the scatterers.

Figure 9:
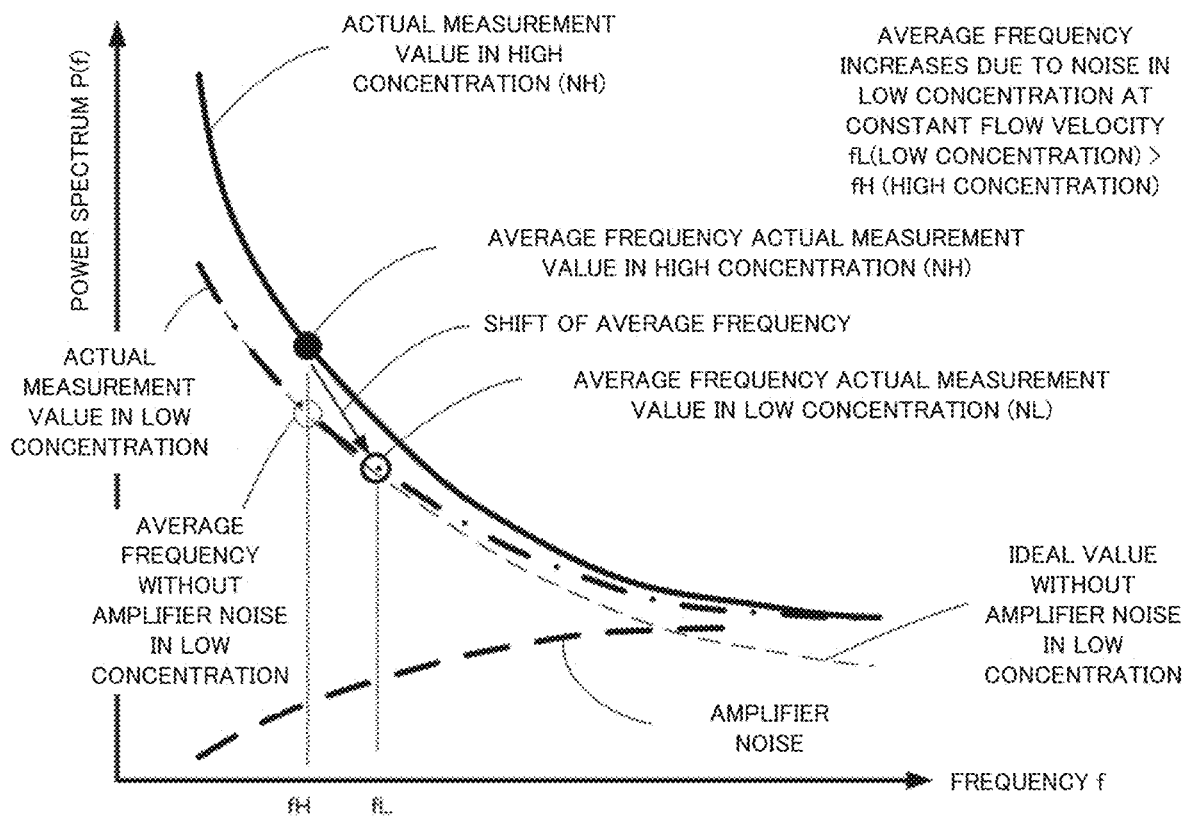
FIG. 9 is a diagram illustrating an example of actual measurement values obtained by actually measuring the power spectrum P(f) of a beat signal, which is measured at a constant velocity of a fluid, for a plurality of fluid concentrations.

A reason why the average frequency fm depends on the concentration of the fluid including the scatterers will be explained with reference to FIG. 9. In FIG. 9, a solid line indicates an actual measurement value of a high concentration fluid, and an alternate long and short dash line indicates an actual measurement value of a low concentration fluid. Moreover, a thick dashed line indicates an amplifier noise, and a thin dashed line indicates a theoretical value for the low concentration fluid without the amplifier noise.

In the amplifier noise, a noise generated by the transimpedance amplifier at the first stage of the amplifier is dominant. The amplifier noise increases with increasing frequency. The amplifier noise is related to a parasitic capacitance of an amplifier input terminal. The amplifier noise has a frequency characteristic that is a differential property. Thus, a noise power increases with increasing frequency.

When the fluid has a high concentration, the number per unit volume of the scatterers included in the fluid increases. Thus, a power of the beat signal measured increases all over the frequencies. On the other hand, when the fluid has a low concentration, the number per unit volume of the scatterers included in the fluid decreases. Thus, the power of the beat signal measured decreases all over the frequencies.

The amplifier noise does not depend on the power of the beat signal. Thus, the low concentration fluid in which the beat signal has a relatively small power is relatively significantly influenced by the amplifier noise, and the power of the beat signal increases in appearance particularly in a high frequency area. On the other hand, the high concentration fluid in which the beat signal has a relatively large power is hardly influenced by the amplifier noise.

Since the velocity of the fluid is set constant, in theory, the average frequency fm, which is proportional to the velocity of the fluid, is constant even if the concentration of the fluid changes. Due to the amplifier noise, however, an average frequency obtained from the actual measurement value for the high concentration fluid (refer to a black circle in FIG. 9) is different from an average frequency obtained from the actual measurement value for the low concentration fluid (refer to a thick white circle in FIG. 9) (if there is no influence of the amplifier noise, the average frequency of the low concentration fluid has a value illustrated by a thin white circle in FIG. 9).

So as to reduce the influence of the amplifier noise, a countermeasure of increasing the power of the semiconductor laser 11 is conceivable, but also may affect adversely, such as, for example, increasing power consumption and adversely affecting eyes of an operator or a subject. In other words, since there is a limit in increasing the power of the semiconductor laser 11 from the viewpoint of safety and power consumption, it is not possible to completely remove the influence of the amplifier noise.

Figure 10:
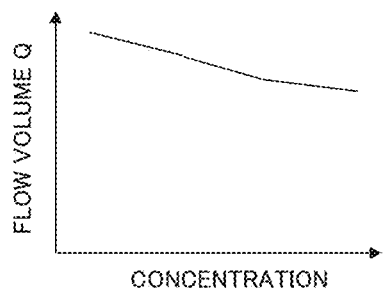
FIG. 10(a) is a diagram illustrating an example of an estimation result when the flow volume Q is estimated only from the average frequency.
FIG. 10(b) is a diagram illustrating an example of the estimation result when the flow volume Q is estimated from the transmitted light amount and the average frequency.
Figure 10:
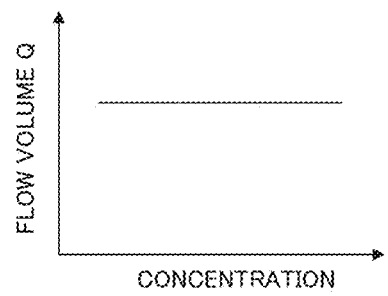

As a result, if the flow volume of the fluid is obtained only from the average frequency fm when only the concentration of the fluid is changed while the flow volume of the fluid is kept constant, then, as illustrated in FIG. 10(*a*), the flow volume of the low concentration fluid, which is easily influenced by the amplifier noise, becomes greater than an actual flow volume.

A reason why the transmitted light amount TDC depends on the flow velocity of the fluid including the scatterers is as follows; namely, when the fluid has a high flow velocity, the number of the scatterers that pass in a predetermined range per unit time increases, and the transmitted light amount TDC thus decreases. On the other hand, when the fluid has a low flow velocity, the number of the scatterers that pass in the predetermined range per unit time decreases, and the transmitted light amount TDC thus increases.

Figure 11:
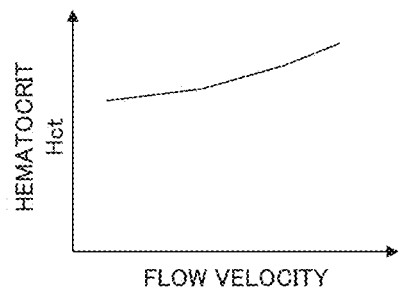
FIG. 11(a) is a diagram illustrating an example of an estimation result when the hematocrit value Ht is estimated only from the transmitted light amount.
FIG. 11(b) is a diagram illustrating an example of the estimation result when the hematocrit value Ht is estimated from the transmitted light amount and the average frequency.
Figure 11:
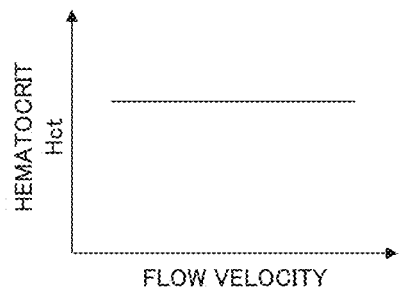

As a result, if the concentration of the fluid is obtained only from the transmitted light amount TDC when only the flow velocity of the fluid is changed while the concentration of the fluid is kept constant, then, as illustrated in FIG. 11(*a*), the concentration of fluid becomes greater than an actual concentration as the flow velocity of the fluid increases.

(Estimation of Fluid Flow Volume and Fluid Concentration)

Next, the fluid evaluation according to the practical example will be explained. As described above, both the average frequency fm and the transmitted light amount TDC depend on the flow velocity and the concentration of the fluid. The present inventors have arrived at such an idea that at least one of the flow volume (or flow velocity) of the fluid and the hematocrit value of the blood, which is the concentration of the fluid, is obtained on the basis of the average frequency fm and the transmitted light amount TDC.

Figure 12:
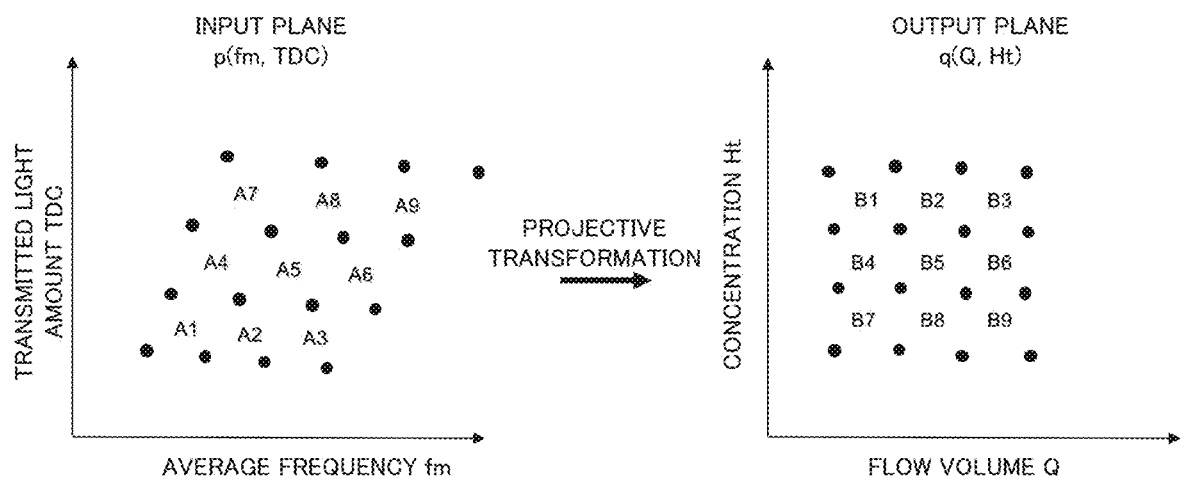
FIG. 12 is a conceptual diagram illustrating a concept of projective transformation according to the practical example.

Particularly in the practical example, as illustrated in FIG. 12, projective transformation from an input plane, which is defined by the average frequency fm and the transmitted light amount TDC, to an output plane, which is defined by the flow volume Q and the concentration Ht (i.e., the hematocrit value), is used to two-dimensionally estimate at least one of the flow volume and the concentration.

A plurality of black circles on each of the input plane and the output plane in FIG. 12 indicate lattice points. An input lattice point, which is a lattice point on the input plane, corresponds to an output lattice point, which is a lattice point on the output plane, in a one-to-one manner, and this correspondence information is stored in advance in the fluid concentration estimator 25.

The average frequency fm and the flow volume Q are proportional to each other (refer to FIG. 7), and the transmitted light amount TDC and the concentration Ht are inversely proportional to each other (refer to FIG. 8). Thus, for example, an input lattice point at the upper left of the input plane corresponds to an output lattice point at the lower left of the output plane. In the same manner, an input lattice point at the lower right of the input plane corresponds to an output lattice point at the upper right of the output plane.

Therefore, for example, an input lattice point area A1, which is defined by four input lattice points on the input plane, corresponds to an output lattice point area B1, which is defined by four output lattice points respectively corresponding to the four input lattice points, on the output plane. In the same manner, input lattice point areas A2 to A9 respectively correspond to output lattice point areas B2 to B9. The input lattice point areas A1 to A9 are different in a shape and an area from each other, due to a non-linear correspondence between the average frequency fm and the transmitted light amount TDC, and the flow volume Q and the concentration Ht.

A transformation coefficient associated with the projective transformation for outputting an input point p(fm, TDC) in each of the input lattice point areas A1 to A9 as an output point q(Q, Ht) in respective one of the output lattice point areas B1 to B9, is stored in advance in the fluid concentration estimator 25 as the transformation coefficient table 253 (refer to FIG. 4).

Now, a method of estimating the flow volume and the concentration according to the practical example will be explained with reference to FIG. 4. In FIG. 4, the input lattice point area determinator 252 of the fluid concentration estimator 25 is configured to determine which of the input lattice point areas A1 to A9 the input point p(fm, TDC) with the average frequency fm and the transmitted light amount TDC as components corresponds to, and is configured to output an area number (i.e., any of A1 to A9) indicating the corresponding input lattice point area.

The projective transformer 254 of the fluid concentration estimator 25 is configured to perform the projective transformation on the average frequency fm and the transmitted light amount TDC by using the transformation coefficient obtained from the transformation coefficient table 253 on the basis of the area number outputted from the input lattice point area determinator 252, and is configured to estimate at least one of the flow volume Q and the concentration Ht.

The transformation coefficient table 253 may be established, for example, in the following manner. For a fluid whose flow volume and concentration are both known, the average frequency and the transmitted light mount may be actually measured in the same manner as in the fluid evaluation apparatus 100 while at least one of the flow volume and the concentration is changed, and the transformation coefficient table 253 may be established on the basis of the correspondence between the flow volume and the concentration, and the average frequency and the transmitted light amount.

It is possible to configure the transformation coefficient associated with the projective transformation to be obtained at each time of the measurement of the target to be measured; however, from the viewpoint of reducing a processing time, the transformation coefficient table 253 is desirably used. In addition, the use of the transformation coefficient table 253 makes it possible to use an inexpensive processor with a relatively low throughput or processing capability for the fluid evaluation apparatus 100, and for example, this allows a product cost to be reduced.

(Input Lattice Point Area Determination)

Next, a specific example of an area determination method of determining which of the input lattice point areas A1 to A9 the input point p(fm, TDC) with the average frequency fm and the transmitted light amount TDC as the components corresponds to will be explained with reference to FIG. 13 and flowcharts in FIG. 14 to FIG. 17.

Figure 13:
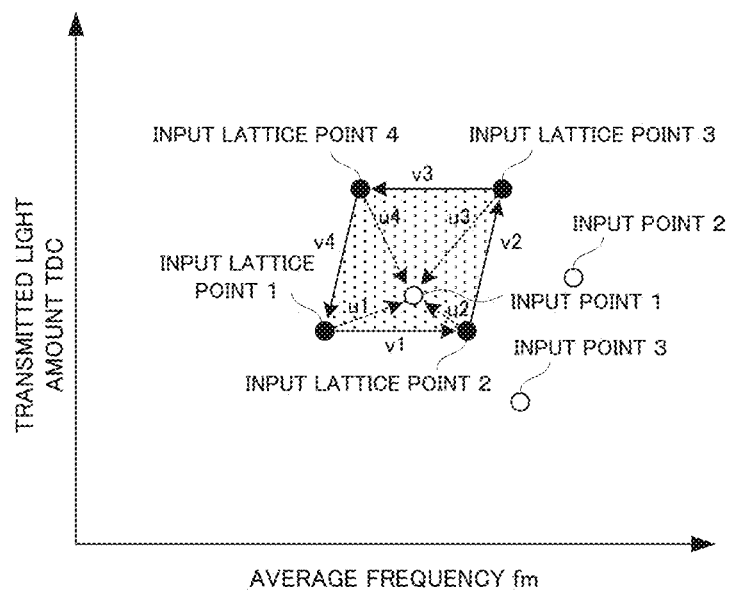
FIG. 13 is a diagram for explaining area determination according to the practical example.

Precondition In FIG. 13, in an input lattice point area defined by input lattice points 1 to 4 (a hatching part), a vector directed from the input lattice point 1 to the input lattice point 2 is set as a vector v1. In the same manner, a vector directed from the input lattice point 2 to the input lattice point 3 is set as a vector v2, a vector directed from the input lattice point 3 to the input lattice point 4 is set as a vector v3, and a vector directed from the input lattice point 4 to the input lattice point 1 is set as a vector v4.

For example, if area determination is performed on an input point 1, the input lattice point area determinator 252 may obtain (i) an outer product of the vector v1 and a vector u1 (i.e., v1×u1), wherein u1 is a vector directed from the input lattice point 1 to the input point 1, (ii) an outer product of the vector v2 and a vector u2 (i.e., v2×u2), wherein u2 is a vector directed from the input lattice point 2 to the input point 1, (iii) an outer product of the vector v3 and a vector u3 (i.e., v3×u3), wherein u3 is a vector directed from the input lattice point 3 to the input point 1, and (iv) an outer product of the vector v4 and a vector u4 (i.e., v4×u4), wherein u4 is a vector directed from the input lattice point 4 to the input point 1, regarding the input lattice point area defined by the input lattice points 1 to 4.

Here, "v1×u1" with a negative value means that the input point 1 is located above a straight line passing through the input lattice point 1 and the input lattice point 2 on the input plane. On the other hand, "v1×u1" with a positive value means that the input point 1 is located under the straight line passing through the input lattice point 1 and the input lattice point 2 on the input plane.

"v2×u2" with a negative value means that the input point 1 is located on the left side of a straight line passing through the input lattice point 2 and the input lattice point 3 on the input plane. On the other hand, "v2×u2" with a positive value means that the input point 1 is located on the right side of the straight line passing through the input lattice point 2 and the input lattice point 3 on the input plane.

"v3×u3" with a negative value means that the input point 1 is located under a straight line passing through the input lattice point 3 and the input lattice point 4 on the input plane. On the other hand, "v3×u3" with a positive value means that the input point 1 is located above the straight line passing through the input lattice point 3 and the input lattice point 4 on the input plane.

"v4×u4" with a negative value means that the input point 1 is located on the right side of a straight line passing through the input lattice point 4 and the input lattice point 1 on the input plane. On the other hand, "v4×u4" with a positive value means that the input point 1 is located on the left side of the straight line passing through the input lattice point 4 and the input lattice point 1 on the input plane.

In other words, it can be said that if all the outer products of the vectors v1 to v4 and the corresponding vectors u1 to u4 results in negative values, the input point 1 is within the input lattice point area defined by the input lattice points 1 to 4. Conversely, it can be said that if there is even a single positive value as the results of the outer products of the vectors v1 to v4 and the corresponding vectors u1 to u4, the input point 1 is not within the input lattice point area defined by the input lattice points 1 to 4.

Specifically, for example, in FIG. 13, an outer product of the vector v2 and a vector directed from the input lattice point 2 to an input point 2 is a positive value (because the input point 2 is located on the right side of the straight line passing through the input lattice point 2 and the input lattice point 3 on the input plane). Alternatively, an outer product of the vector v1 and a vector directed from the input lattice point 1 to an input point 3 is a positive value (because the input point 3 is located under the straight line passing through the input lattice point 1 and the input lattice point 2 on the input plane).

Area Determination Method (Basic Form)

Figure 14:
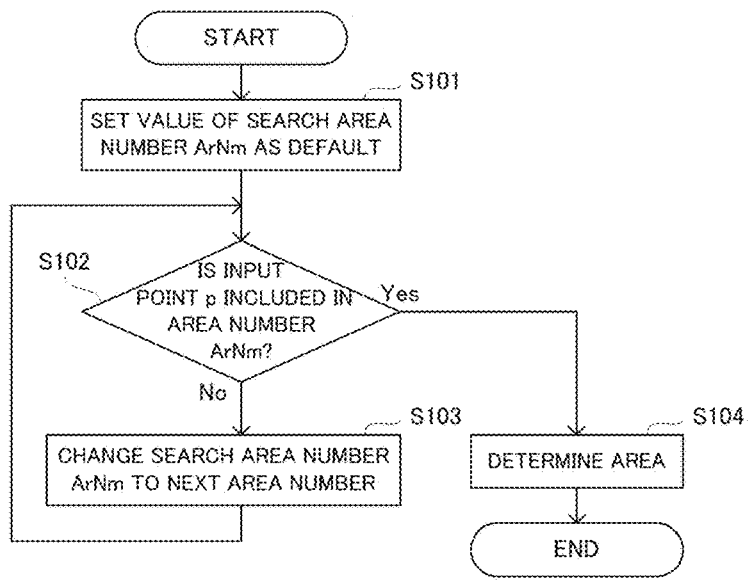
FIG. 14 is a flowchart illustrating an area determination process according to the practical example.

In an area determination method illustrated in FIG. 14, firstly, the input lattice point area determinator 252 sets a preset initial value (or a default value) for a search area number ArNm (step S101). The input lattice point area determinator 252 then obtains an outer product in the aforementioned manner from the input point p and four input lattice points that define an input lattice point area indicated by the search area number ArNm, and determines whether or not the input point p is included in the input lattice point area indicated by the search area number ArNm (step S102).

In the determination in the step S102, if it is determined that the input point p is included in the input lattice point area indicated by the search area number ArNm (the step S102: Yes), the input lattice point area determinator 252 outputs the search area number ArNm as the area number ArNm (refer to FIG. 4) (step S104). The input lattice point area determinator 252 then performs the step S101 again after a lapse of a first predetermined period.

On the other hand, in the determination in the step S102, if it is determined that the input point p is not included in the input lattice point area indicated by the search area number ArNm (the step S102: No), the input lattice point area determinator 252 changes the search area number ArNm to a number indicating an input lattice point area to be searched next (step S103), and performs the step S102.

Area Determination Method (First Modified Example)

Figure 15:
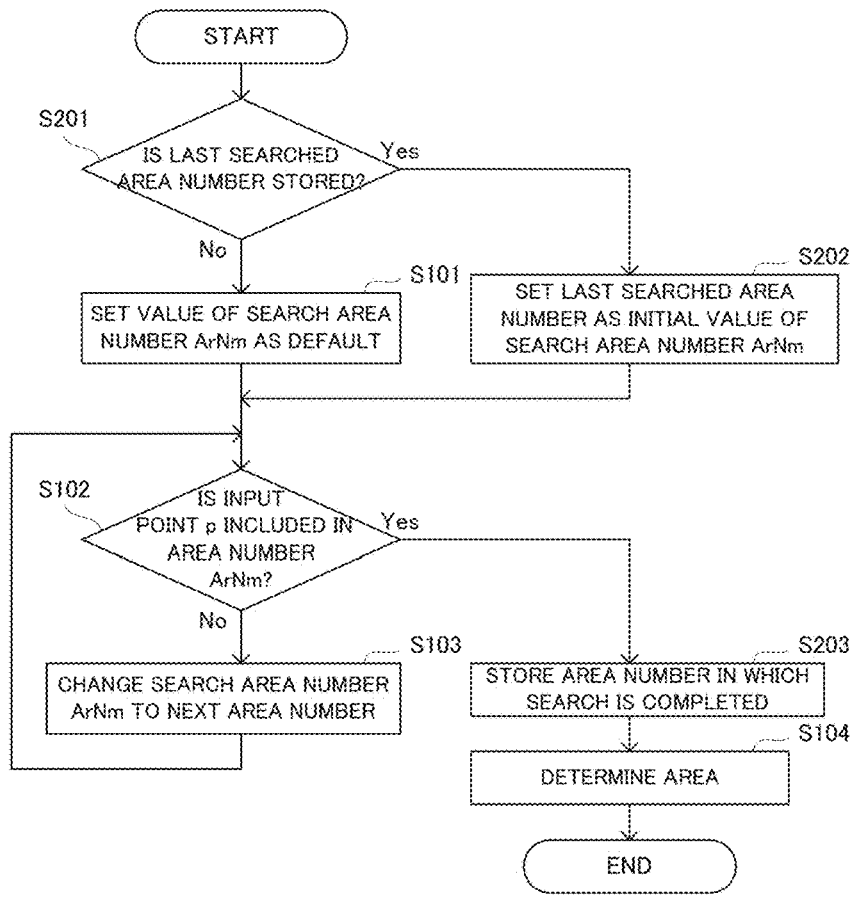
FIG. 15 is a flowchart illustrating a first modified example of the area determination process according to the practical example.

In an area determination method illustrated in FIG. 15, the input lattice point area determinator 252 is configured to store a number indicating the last searched input lattice point area, for example, in a memory or the like, at the last time of performing the area determination.

In FIG. 15, firstly, the input lattice point area determinator 252 determines whether or not the number indicating the last searched input lattice point area is stored at the last time of performing the area determination (step S201). In this determination, if it is determined that the number indicating the input lattice point area is stored (the step S201: Yes), the input lattice point area determinator 252 sets the stored number as the search area number ArNm (step S202). On the other hand, in this determination, if it is determined that the number indicating the input lattice point area is not stored (the step S201: No), the step S101 is performed.

In the determination in the step S102, if it is determined that the input point p is included in the input lattice point area indicated by the search area number ArNm (the step S102: Yes), the input lattice point area determinator 252 stores (or updates) the search area number ArNm (step S203), and performs the step S104. The input lattice point area determinator 252 then performs the step S101 again after a lapse of the first predetermined period.

Area Determination Method (Second Modified Example)

Figure 16:
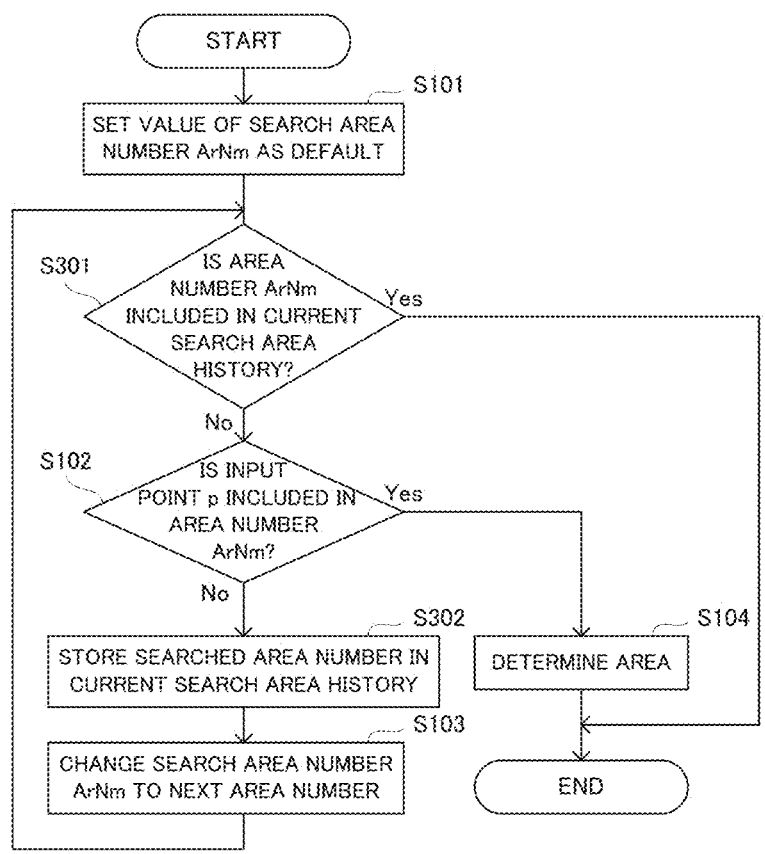
FIG. 16 is a flowchart illustrating a second modified example of the area determination process according to the practical example.

In an area determination method illustrated in FIG. 16, the input lattice point area determinator 252 is configured to store a number indicating an input lattice point area on which the area determination is currently performed (i.e., searched), for example, in the memory or the like, as a search area history.

In FIG. 16, the input lattice point area determinator 252 determines whether or not a number corresponding to a currently set search area number ArNm is included in a current search area history, after the step S101 (step S301). In this determination, if it is determined that the number corresponding to the currently set search area number ArNm is not included (the step S301: No), the determination in the step S102 is performed.

In the determination in the step S102, if it is determined that the input point p is not included in the input lattice point area indicated by the search area number ArNm (the step S102: No), the input lattice point area determinator 252 stores the search area number ArNm in the current search area history (step S302), and performs the step S103. In the step S103, the number that is not included in the current search area history is desirably selected as a number indicating an input lattice point area to be searched next.

On the other hand, in the determination in the step S102, if it is determined that the input point p is included in the input lattice point area indicated by the search area number ArNm (the step S102: Yes), the step S104 is performed. The input lattice point area determinator 252 then performs the step S101 again after a lapse of the first predetermined period.

In the step S301, if it is determined that the number corresponding to the currently set search area number ArNm is included in the current search area history (the step S301: Yes), the process illustrated in FIG. 16 is ended. The input lattice point area determinator 252 then performs the step S101 again after a lapse of a second predetermined period.

By virtue of such a configuration, it is possible to prevent the same process from being repeatedly performed on the input lattice point area that is determined, already once, not to include the input point p.

Area Determination Method (Third Modified Example)

Figure 17:
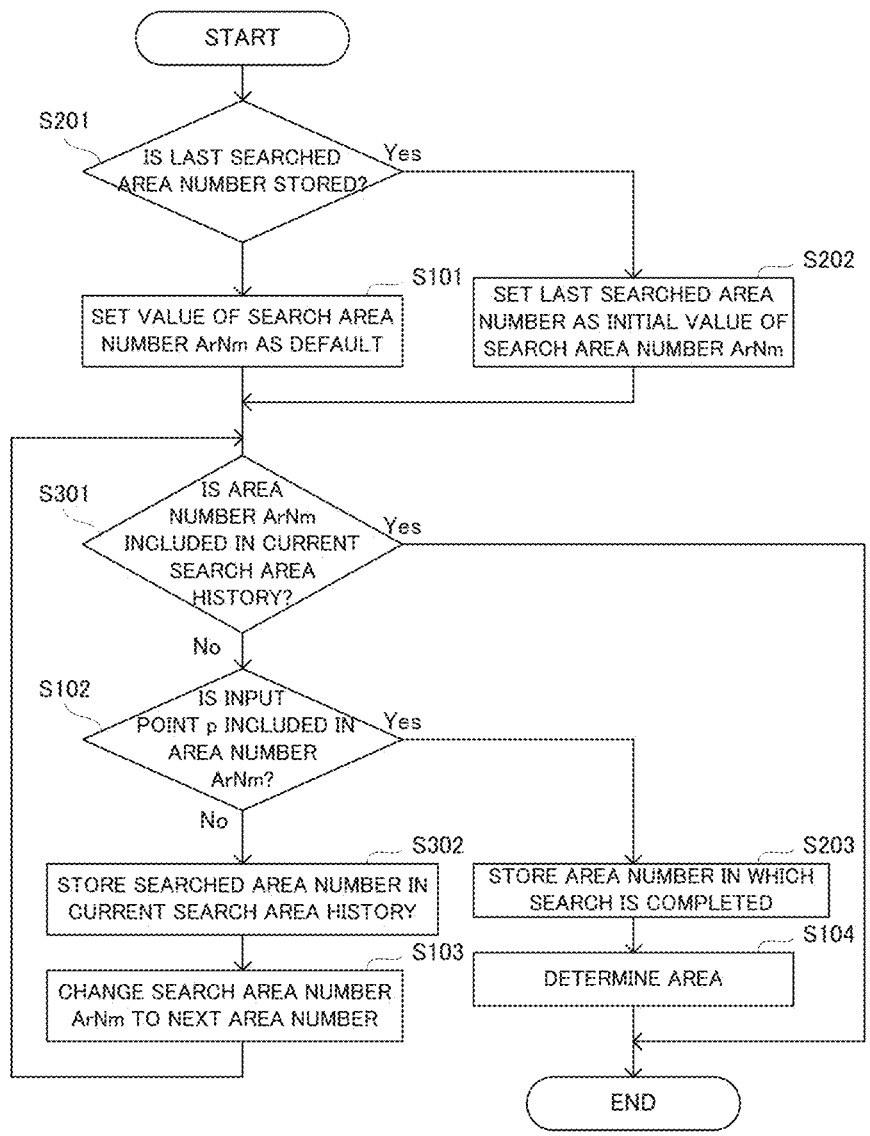
FIG. 17 is a flowchart illustrating a third modified example of the area determination process according to the practical example.

In an area determination method illustrated in FIG. 17, the input lattice point area determinator 252 is configured (i) to store the number indicating the last searched input lattice point area, for example, in the memory or the like, at the last time of performing the area determination, and (ii) to store the number indicating the input lattice point area on which the area determination is currently performed, for example, in the memory or the like, as the search area history.

In FIG. 17, in the determination in the step S201, if it is determined that the number indicating the input lattice point area is stored (the step S201: Yes), the input lattice point area determinator 252 performs the step S202. On the other hand, in the determination in the step S201, if it is determined that the number indicating the input lattice point area is not stored (the step S201: No), the step S101 is performed.

After the step S202 or the step S101, the input lattice point area determinator 252 performs the step S301. In this determination, if it is determined that the number corresponding to the currently set search area number ArNm is included in the current search area history (the step S301: Yes), the process illustrated in FIG. 17 is ended. The input lattice point area determinator 252 then performs the step S101 again after a lapse of the second predetermined period.

On the other hand, if it is determined that the number corresponding to the currently set search area number ArNm is not included (the step S301: No), the determination in the step S102 is performed. In this determination, if it is determined that the input point p is not included in the input lattice point area indicated by the search area number ArNm (the step S102: No), the step S302 and the step S103 are performed.

On the other hand, in the determination in the step S102, if it is determined that the input point p is included in the input lattice point area indicated by the search area number ArNm (the step S102: Yes), the input lattice point area determinator 252 stores (or updates) the search area number ArNm (the step S203), and performs the step S104. The input lattice point area determinator 252 then performs the step S101 again after a lapse of the first predetermined period.

(Technical Effect)

On the fluid evaluation apparatus 100, the input point p(fm, TDC) on the input plane is mapped to the output point q(Q, Ht) on the output plane, by the projective transformation. Thus, according to the fluid evaluation apparatus 100, for example, even if only the concentration of the blood is changed while the flow volume of the blood is kept constant, it is possible to perform appropriate evaluation without any influence of the change in the concentration of the blood, as illustrated in FIG. 10(b). In the same manner, for example, even if only the flow velocity of the blood is changed while the concentration of the blood is kept constant, it is possible to perform appropriate evaluation without any influence of the change in the flow velocity of the blood, as illustrated in FIG. 11(b).

As illustrated in FIG. 12, out of four input lattice points that define the input lattice point area A5, two input lattice points on the right side also define the input lattice point area A6 adjacent to the input lattice point area A5. In other words, on the input plane, the input lattice point areas A1 to A9 are arranged without any gap between adjacent areas. As a result, on the output plane, the output lattice point areas B1 to B9 are also arranged without any gap between adjacent areas.

The input plane illustrated in FIG. 12 includes the nine input lattice point areas A1 to A9, but may include 10 or more input lattice point areas. As the number of the input lattice point areas increases, an estimation error associated with the fluid evaluation apparatus 100 can be further reduced. On the other hand, if the input plane is defined by the average frequency and a value of a logarithm of the transmitted light amount TDC, a correspondence between the average frequency fm and the value of the logarithm of the transmitted light amount TDC, and the flow volume Q and the concentration Ht has higher linearity than the correspondence between the average frequency fm and the transmitted light amount TDC, and the flow volume Q and the concentration Ht. Thus, even if the number of the input lattice point areas is less than nine, the estimation error of the fluid evaluation apparatus 100 can be reduced.

The "semiconductor laser 11", the "light receiving elements 21 and 31", the "fluid concentration estimator 25" according to the practical example are respectively an example of the "irradiator", the "light receiver", and the "estimator" according to the present invention. The "transmitted light amount TDC", the "average frequency fm", the "input plane", and the "output plane" according to the practical example are respectively an example of the "light amount information", the "frequency information", the "first plane", and the "second plane" according to the present invention.

(Modified Examples)

Figure 18:
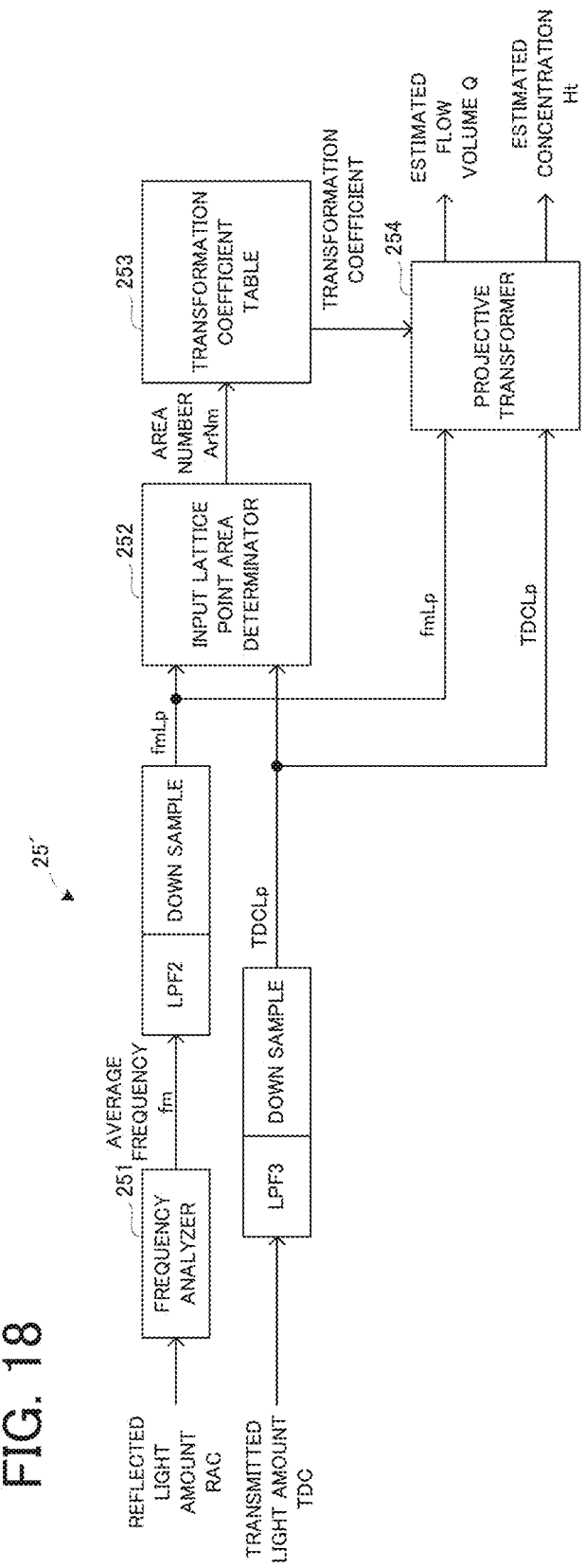
FIG. 18 is a block diagram illustrating a configuration of a modified example of the fluid concentration estimator according to the practical example.

A modified example of the fluid evaluation apparatus 100 according to the practical example will be explained with reference to FIG. 18. FIG. 18 is a block diagram illustrating a configuration of the modified example of the fluid concentration estimator according to the practical example.

In FIG. 18, in a fluid concentration estimator 25', the average frequency fm outputted from the frequency analyzer 251 is averaged via an LPF2, and then, an average frequency fmLp, which is the average frequency fm with a sampling rate reduced, is outputted from a down sample. In the same manner, the transmitted light amount TDC outputted from the A/D converter 34 is averaged via an LPF3, and then, a transmitted light amount TDCLp, which is the transmitted light amount TDC with a sampling rate reduced, is outputted from a down sample.

The input lattice point area determinator 252 may use an input point p with the average frequency fmLp and the transmitted light amount TDCLp as components, to determine the input lattice point area. The projective transformer 254 may estimate at least one of the flow volume Q and the concentration Ht on the basis of the average frequency fmLp and the transmitted light amount TDCLp.

By virtue of such a configuration, a data rate of data inputted to the input lattice point area determinator 252 is reduced, so that a determination period can be prolonged or increased. Thus, for example, (i) when the input lattice point area determinator 252 is realized by a relatively slow processor or (ii) when the number of the input lattice point areas is increased to improve estimation accuracy (or to reduce the estimation error), it is possible to prevent a real-time property of the flow volume estimation and/or the concentration estimation from being damaged.

The fluid evaluation apparatus according to the present invention can be also applied to, for example, evaluation of a blood that flows in a blood vessel of a living body, or evaluation of an arbitrary fluid other than the blood (e.g., ink, oil, wastewater, seasonings, etc.).

The present invention is not limited to the aforementioned embodiments and examples, but various changes may be made, if desired, without departing from the essence or spirit of the invention which can be read from the claims and the entire specification. A fluid evaluation apparatus, a fluid evaluation method, a computer program, and a recording medium that involve such changes are also intended to be within the technical scope of the present invention.

DESCRIPTION OF REFERENCE NUMERALS AND LETTERS 11 semiconductor laser
12 laser driver
21, 31 light receiving element
22, 32 I-V converter
23 BPF amplifier
24, 34 A/D converter
25 fluid concentration estimator
33 LPF amplifier
100 fluid evaluation apparatus
251 frequency analyzer
252 input lattice point area determinator
253 transformation coefficient table
254 projective transformer

The invention claimed is:

1. A fluid evaluation apparatus comprising:
    an irradiator configured to irradiate a fluid with light;
    a light receiver configured to receive scattered light from the fluid and configured to output a light receiving signal; and
    an estimator configured to map an input point, that is on a first plane defined by a light amount and a frequency, on a second plane defined by a flow volume of the fluid and a concentration of the fluid by transformation to determine at least one of the flow volume and the concentration corresponding to the mapped input point by transformation,
    wherein the light amount and the frequency are respectively indicated by light amount information, which indicates the light amount of the scattered light included in the light receiving signal, and by frequency information, which indicates the frequency associated with a beat signal caused by a Doppler shift of the light included in the light receiving signal.

2. The fluid evaluation apparatus according to claim 1, wherein said estimator
    has lattice point information associated with a plurality of lattice points each of which has a known correspondence between a position indicated by the light amount and the frequency on the first plane and a position indicated by the flow volume and the concentration on the second plane, and
    is configured to map the input point on the second plane, based on a positional relation between the input point on the first plane and a lattice point indicated by the lattice point information.

3. The fluid evaluation apparatus according to claim 2, wherein said estimator is configured to specify an area to which the input point belongs, from among one or a plurality of areas defined by a plurality of lattice points indicated by the lattice point information from the positional relation, and is configured to map the input point on the second plane by using a transformation coefficient according to the specified area.

4. The fluid evaluation apparatus according to claim 1, wherein
said light receiver has a first light receiver configured to receive scattered light that is reflected by the fluid, out of the scattered light, and a second light receiver configured to receive scattered light that is transmitted through the fluid, out of the scattered light, and
said estimator is configured to obtain the frequency information from an output signal of the first light receiver, which is a part of the light receiving signal, and is configured to obtain the light amount information from an output signal of the second light receiver, which is another part of the light receiving signal.

5. A fluid evaluation method in a fluid evaluation apparatus including: an irradiator configured to irradiate a fluid with light, and a light receiver configured to receive scattered light from the fluid and configured to output a light receiving signal, said fluid evaluation method comprising:
mapping an input point, that is on a first plane defined by a light amount and a frequency, on a second plane defined by a flow volume of the fluid and a concentration of the fluid by transformation to determine at least one of the flow volume and the concentration,
wherein the light amount and the frequency are respectively indicated by light amount information, which indicates the light amount of the scattered light included in the light receiving signal, and by frequency information, which indicates the frequency associated with a beat signal caused by a Doppler shift of the light included in the light receiving signal.

6. A non-transitory computer readable medium recording a computer program for making a computer, which is provided in a fluid evaluation apparatus including: an irradiator configured to irradiate a fluid with light, and a light receiver configured to receive scattered light from the fluid and configured to output a light receiving signal, perform a method comprising:
mapping an input point, that is on a first plane defined by a light amount and a frequency, on a second plane defined by a flow volume of the fluid and a concentration of the fluid by transformation to determine at least one of the flow volume and the concentration,
wherein the light amount and the frequency are respectively indicated by light amount information, which indicates the light amount of the scattered light included in the light receiving signal, and by frequency information, which indicates the frequency associated with a beat signal caused by a Doppler shift of the light included in the light receiving signal.

7. A fluid evaluation apparatus comprising:
an irradiator configured to irradiate a fluid with light;
a light receiver configured to receive scattered light from the fluid and configured to output a light receiving signal; and
an estimator configured to transform a first parameter with light amount information and frequency information as components, to a second parameter with a flow volume of the fluid and a concentration of the fluid as components, thereby estimating at least one of the flow volume and the concentration,
wherein the light amount information indicates a light amount of the scattered light included in the light receiving signal, and the frequency information indicates a frequency associated with a beat signal caused by a Doppler shift of the light included in the light receiving signal.

* * * * *